United States Patent
Goodman

[11] Patent Number: 5,827,061
[45] Date of Patent: Oct. 27, 1998

[54] DENTAL BITE BLOCK WITH ASPIRATOR TIPS

[76] Inventor: Phillip M. Goodman, 534 Sugarbrook Tr., Bellbrook, Ohio 45305

[21] Appl. No.: 850,755

[22] Filed: May 2, 1997

[51] Int. Cl.⁶ ................................................ A61C 17/06
[52] U.S. Cl. ................................................................ 433/93
[58] Field of Search .................................. 433/91, 92, 93, 433/94, 95, 136, 137, 138, 139, 140

[56] References Cited

U.S. PATENT DOCUMENTS

| | | | |
|---|---|---|---|
| 2,823,455 | 2/1958 | Sprague | 433/93 |
| 3,924,333 | 12/1975 | Erickson | 433/93 |
| 4,325,695 | 4/1982 | Sundelin et al. | 433/91 |
| 4,975,057 | 12/1990 | Dyfvermark | 433/91 |
| 4,992,046 | 2/1991 | Sharp | 433/93 |
| 5,071,347 | 12/1991 | McGuire | 433/91 |
| 5,078,602 | 1/1992 | Honoshofsky | 433/91 |
| 5,152,656 | 10/1992 | Duggan et al. | 433/93 |

*Primary Examiner*—Nicholas D. Lucchesi
*Attorney, Agent, or Firm*—Patent & Trade Mark Services; Joseph H. McGlynn

[57] ABSTRACT

An improved dental apparatus for removing excess saliva during dental procedures and also for maintaining a patient's jaw comfortably in an open position. A dental bite block has occlusal resting portions joined by an arcuate anterior member. One occlusal resting portion has a main vacuum port extending angularly therefrom and communicating with a hollow channel having openings on opposing lateral surfaces of said occlusal resting portion. The main vacuum port operably receives the suction hose of a vacuum evacuation system. Lingual and buccal saliva ejector ports, each having circumferential grooved attachments and nozzle portions, are communicably connected to either opening on the occlusal resting portion. Saliva is communicated from the ejector ports into the main port, whereupon it is communicated into the vacuum system for dispensation.

5 Claims, 2 Drawing Sheets

DENTAL BITE BLOCK WITH ASPIRATOR TIPS

BACKGROUND OF THE INVENTION

The present invention relates generally to dental appliances for removing saliva from the mouth during dental procedures, and more particularly to a bite block having suction ports for the removal of saliva and other features which ease the discomfort and difficulty of dental procedures.

DESCRIPTION OF THE PRIOR ART

It is known in the art of dentistry to have devices for removing saliva from a patient's mouth during dental procedures. However, as described in more detail below, the prior art devices tend to cause patient discomfort and to hinder the dental professional's visibility of the patient's mouth.

U.S. Pat. No. 5,071,347 describes a device for removing saliva having absorbent rolls supported on a pair of suction tubes. This device is uncomfortable for the patient, requiring a jaw clamp to hold the absorbent rolls against the patient's gum. The suction tubes also obstruct the dentist's visibility and access, as the tubes intersect at a point directly in the dentist's line of sight.

U.S. Pat. No. 5,078,602 discloses a saliva ejector having a hollow tube operably associated with a tongue protector and connected to a vacuum system. This device, as well, is uncomfortable for the patient, providing no means for holding the patient's mouth open and thereby inducing mandibular fatigue.

U.S. Pat. No. 4,325,695 describes a suction operated dental saliva ejector having a perforated suction wall. This device employs a jaw clamp that is uncomfortable for the patient. It also lacks a means for holding the patient's jaw open.

U.S. Pat. No. 4,975,057 discloses a bite block with an evacuation nozzle. This device is uncomfortable for the patient, having upstanding ribs which are likely to scrape the gums of the patient. This device is also bulky and obtrusive, hindering the dental professional's visibility and access.

There remains a need in the art for a comfortable and unobtrusive device which can be used to remove excess saliva from a patient's mouth during dental procedures. There also remains a need for a saliva removal device which maintains the patient's mouth in an open position, to reduce mandibular fatigue and to increase visibility. The present invention, described in detail below, overcomes the many disadvantages of the prior art and affords additional benefits not provided by the inventions heretofore disclosed.

SUMMARY OF THE INVENTION

The present invention is an improved dental bite block for use in dental procedures to enhance the comfort of the patient and to make the patient's teeth more visible and accessible to the dental professional. The bite block is adapted for application between the upper and lower jaw of the patient to remove excess saliva and to maintain the patient's jaw in an open position.

The bite block comprises occlusal resting portions connected by an arcuate anterior portion. One occlusal resting portion has an angularly extending main port which is connected to a suction hose in communication with a vacuum system. Lingual and buccal saliva ejector ports are provided on either side of the same occlusal resting portion, and are communicably connected to the main port. Suction applied to the main port therefore causes excess saliva in the buccal and lingual regions to be expelled into the vacuum system.

The present invention enhances patient comfort in several ways. First, it eliminates excess saliva before it accumulates, thereby reducing the discomfort and embarrassment associated with such accumulation. Secondly, it relieves the patient of the need to actively hold his or her mouth open, which reduces mandibular fatigue. Additionally, the arcuate anterior portion of the present invention is contoured to fit the tongue, reducing strain and also eliminating the possibility of triggering the gag reflex. The invention also has benefits for the dental professional, since the patient need not be constantly reminded to "open wide". Moreover, the angular displacement of the main port removes it from the dentist's line of sight, thereby affording increased visibility and access to the patient's oral cavity. The dentist is also relieved of the need to periodically insert a suction tube into the patient's mouth during dental procedures, as is the standard practice in many dental offices.

Accordingly, it is an object of the present invention to provide an improved dental appliance.

It is a further object of this invention to provide a dental appliance which makes dental procedures easier and more comfortable for both patients and dental practitioners.

It is a further object of this invention to provide a dental appliance which automatically removes excess saliva from a patient's mouth during dental procedures.

It is still further an object of this invention to provide a dental appliance which keeps the patient's mouth in the open position during dental procedures.

It is still further an object of this invention to provide a dental appliance in the form of a bite block, having occlusal resting portions, arcuate anterior portion, and ports for the ejection of saliva through vacuum means.

These and other objects and advantages of the present invention will become fully apparent from the detailed description below, when taken in conjunction with the annexed drawings.

DESCRIPTION OF THE PREFERRED EMBODIMENT

Figure 1:
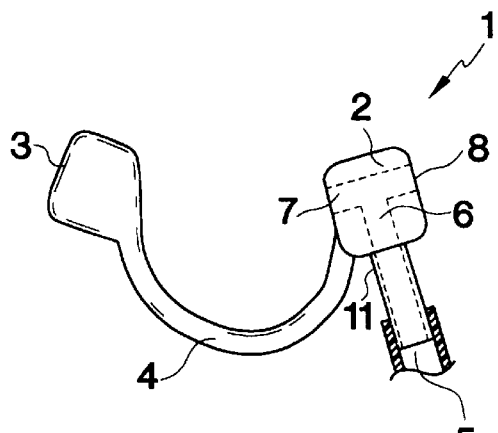
FIG. 1 shows a top view of the dental bite block, with shadow lines representing obscured portions.

Referring now to the drawings in greater detail, it can be seen in FIG. 1 that the bite block 1 of the present invention includes occlusal resting portions 2, 3 connected by an arcuate anterior member 4. Though dimensions may vary, the distance between the outer lateral surfaces of the occlusal resting portions 2, 3 is approximately 2", while the distance between the back surfaces of the occlusal resting portions and the front of the anterior member is approximately 1".

Figure 2:
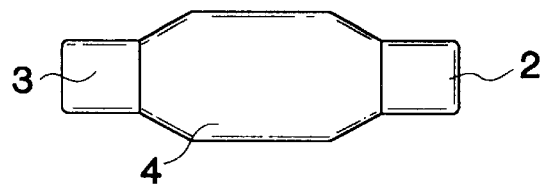
FIG. 2 shows a front elevational view of the dental bite block.

As depicted in FIG. 2, showing a front elevational view of the bite block 1, the anterior member 4 is of somewhat greater height than the occlusal resting surfaces 2, 3, the anterior member being approximately 4" in height, while the occlusal resting portions 2, 3 are approximately 0.875" high. As described in detail below, occlusal resting portions 2, 3 maintain the patient's jaw comfortably in an open position, while the anterior member 4 contours to the patient's tongue and holds it to prevent obstruction during dental procedures.

As depicted in FIG. 1, one occlusal resting portion 2 has disposed thereon a main suction port 5, which consists of a short tubular member capable of operably associating with a vacuum tube 11. Main suction port 5 extends outward at approximately 6 degrees relative to the line defined by the frontmost point of the anterior member 4 and the midpoint between the occlusal resting portions 2, 3. As depicted by the dotted lines in FIG. 1, main suction port 5 communicates with a hollow channel 6 extending through and having openings 7, 8 on either lateral surface of the occlusal resting portion 2.

Figure 3:
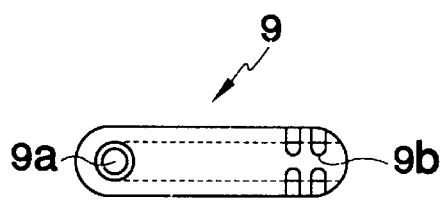
FIG. 3 shows a side view of the lingual saliva ejector port.
Figure 4:
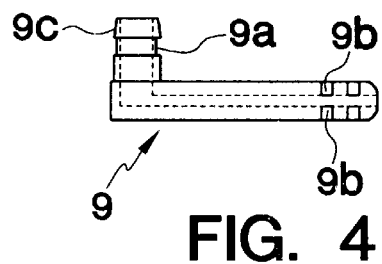
FIG. 4 shows a top view of the lingual saliva ejector port.
Figure 5:
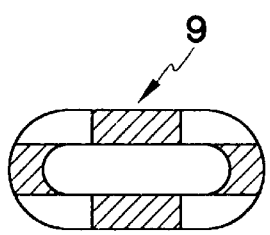
FIG. 5 shows a cross sectional view of the lingual saliva ejector port.

Depicted separately in FIGS. 3–8 are the lingual saliva ejector port 9 and the buccal saliva ejector port 10, which are communicably connected to openings 7, 8 on the occlusal resting portion 2 to transfer saliva to the main port 5. As shown in FIGS. 3–5, the lingual saliva ejector port 9 consists of a tubular piece of flexible plastic approximately 1" in length and approximately 0.135" in diameter. Lingual saliva ejector port 9 has a nozzle 9a at one end, which is approximately 0.4" in length. At the opposite end of the lingual saliva ejector port 9 are circumferential grooves 9b which provide interlocking attachment means to the inside of opening 7 on the occlusal resting portion 2. Nozzle 9a has a similar groove 9c so that the lingual saliva ejector port may be attached at either end to the inside of opening 7. Lingual saliva ejector port 9 serves to remove saliva from the portion of the mouth containing the tongue, where saliva tends to accumulate.

Buccal saliva ejector port 10 (not shown) is identical to the lingual saliva ejector port 9, except that it is somewhat shorter, being approximately 0.68" in length. Buccal saliva ejector port 10 is connected by the means described above to the outside opening 8 of the occlusal resting portion 2, which is adjacent to the cheek area. The buccal saliva ejector port 10 lies in the vestibule of the cheek and channels away saliva which tends to accumulate in that region of the mouth.

To use the bite block 1, the occlusal resting portions 2, 3 are positioned between the upper and lower jaws of the patient prior to the dental procedure. The occlusal resting portions 2, 3 maintain the patient's mouth in the open position, thereby affording greater visibility and avoiding mandibular fatigue. The anterior member 4 thus lies in front of the tongue, forming a contoured fit and also preventing the tongue from obstructing the procedure. A vacuum hose 11 is then connected to the main suction port 5. Accumulated saliva will then be ejected from the lingual and buccal regions through the saliva ejector ports 9, 10 and into the main port 5, whereupon it will be received into the vacuum hose 11 for dispensation into the vacuum system.

Figure 6:
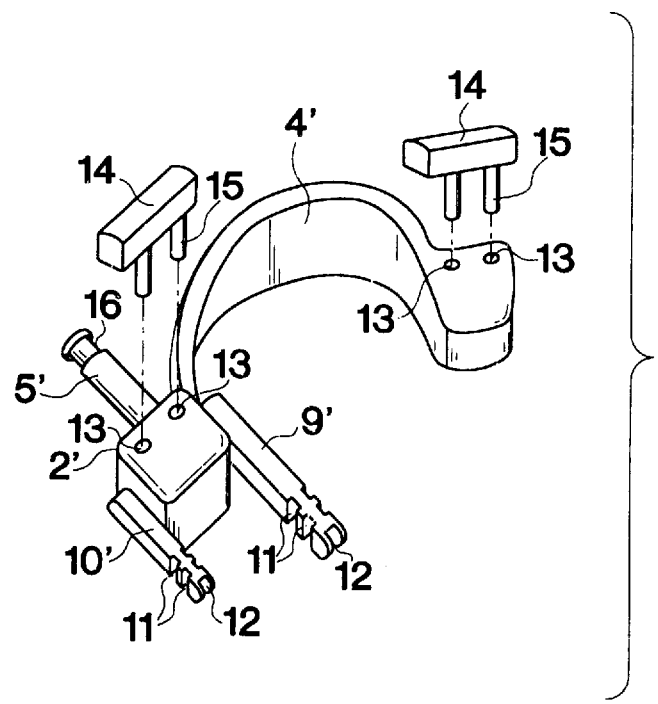
FIG. 6 shows a perspective view of a second embodiment of the present invention.
Figure 7:
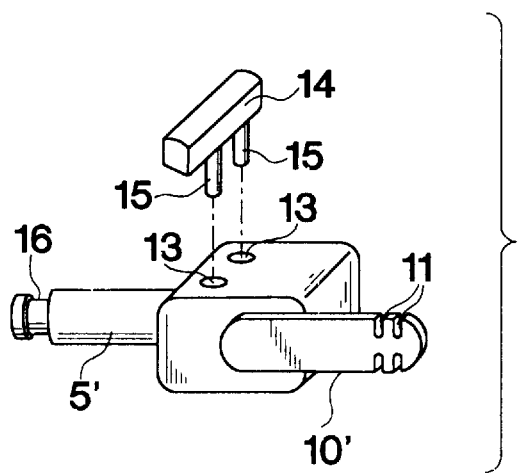
FIG. 7 shows an exploded view of a bite block used with the embodiment of FIG. 6.

The second embodiment of the present invention, shown in FIGS. 6, 7 is similar in function and operation to the FIG. 1 embodiment. It has an anterior member 4', occlusal resting portions 2', 3', main suction port 5', lingual saliva ejector port 9', and buccal saliva ejector port 10', all of which serve the same function as their counterparts in the FIG. 1 embodiment. Main suction port 5' has a groove or channel 16 which will help to secure a vacuum line attached thereto. However, the second embodiment differs in that the occlusal resting portions 2', 3' are provided with apertures 13 which receive the posts 15 attached to bite pads 14, only one of which is shown in FIG. 7.

The bite pads 14 will come in different sizes, such as, but not limited to, 5 mm and 7 mm high. The bite pads can be attached to the occlusal resting portions 2', 3' in order to allow for a wider opening in the patients mouth so that the dentist has easier access for certain dental procedures.

The posts or legs 15 of the bite pads 14 will be made from a soft, resilient material and will fit within the openings 13 in an interference fit. The different sizes of the bite pads will allow the dentist to adjust the size of the opening necessary to perform certain dental procedures.

The usefulness and advantages of the bite block 1 may now be appreciated. The patient is relived of the discomfort and embarrassment of excess saliva accumulation without the need for the dentist to periodically insert a vacuum tube. The patient's mouth is kept in an open position, which relieves discomfort and also affords greater visibility to the dental professional. The present invention thus provides a much needed device whose advantages will be welcomed by both patients and practitioners alike.

Although the dental bite block and the method of using the same according to the present invention has been described in the foregoing specification with considerable details, it is to be understood that modifications may be made to the present invention which do not exceed the scope of the appended claims and modified forms of this invention done by others skilled in the art to which the invention pertains will be considered infringements of this invention when those modified forms fall within the claimed scope of the invention.

What I claim as my invention is:

1. A dental bite block instrument for removing saliva from the mouth of a patient comprising:

a bite block having a curved center portion and an occlusal resting means attached to each end of said curved center section, at least one of said occlusal resting means being hollow, a first port means for attaching a lingual saliva ejector on said at least one occlusal resting means, a second port means for attaching a buccal saliva ejector on said at least one occlusal resting means, a third port means for attaching a vacuum tube to said at least one occlusal resting means, said first, second and third port means communicating with each other.

2. The dental bite block instrument for removing saliva from the mouth of a patient as claimed in claim 1, in combination with a lingual saliva ejector, said lingual saliva ejector being connected to said first port means, said lingual saliva ejector having circumferential grooves means for engaging an interior portion of said first port means and securing said lingual saliva ejector to said first port means.

3. The dental bite block instrument for removing saliva from the mouth of a patient as claimed in claim 1, in combination with a buccal saliva ejector, said buccal saliva ejector being connected to said second port means, said buccal saliva ejector having circumferential grooves means for engaging an interior portion of said second port means and securing said buccal saliva ejector to said second port means.

4. The dental bite block instrument for removing saliva from the mouth of a patient as claimed in claim 1, in combination with a vacuum tube, said vacuum tube being connected to said third port means, said vacuum tube having means for engaging an exterior portion of said third port means and securing said vacuum tube to said third port means.

5. The dental bite block instrument for removing saliva from the mouth of a patient as claimed in claim 1 wherein said occlusal resting means attached to each end of said curved center section each have at least one aperture therein, and bite pads, each having at least one leg attached thereto, said at least one leg on said bite pads engaging said at least one aperture on said occlusal resting means, whereby the dimensions of said occlusal resting means may be changed.

* * * * *